(12) United States Patent
Robin

(10) Patent No.: US 6,742,895 B2
(45) Date of Patent: Jun. 1, 2004

(54) INTERNET-BASED GLAUCOMA DIAGNOSTIC SYSTEM

(76) Inventor: Alan L. Robin, 6628 Charlesway, Towson, MD (US) 21204

( * ) Notice: Subject to any disclaimer, the term of this patent is extended or adjusted under 35 U.S.C. 154(b) by 0 days.

(21) Appl. No.: 09/901,476

(22) Filed: Jul. 9, 2001

(65) Prior Publication Data

US 2002/0005935 A1 Jan. 17, 2002

Related U.S. Application Data

(60) Provisional application No. 60/216,397, filed on Jul. 6, 2000.

(51) Int. Cl.[7] ................................................. A61B 3/00
(52) U.S. Cl. ......................... 351/246; 369/53.1; 705/3
(58) Field of Search ......................... 351/246; 128/898; 369/53.1; D24/107, 172, 185, 186, 231; 600/300; 705/1, 2, 3

(56) References Cited

U.S. PATENT DOCUMENTS

| | | | | |
|---|---|---|---|---|
| 5,910,107 A | * | 6/1999 | Iliff | ............................. 600/300 |
| 6,081,786 A | * | 6/2000 | Barry et al. | ................. 600/300 |
| 6,234,964 B1 | * | 5/2001 | Iliff | ............................. 600/300 |
| 2002/0016720 A1 | * | 2/2002 | Poropatich et al. | ............ 705/3 |
| 2002/0016923 A1 | * | 2/2002 | Knaus et al. | ................... 705/3 |
| 2002/0032583 A1 | * | 3/2002 | Joao | ............................... 705/2 |

* cited by examiner

*Primary Examiner*—George Manuel
*Assistant Examiner*—John R Sanders
(74) *Attorney, Agent, or Firm*—Law Offices of Royal W. Craig

(57) ABSTRACT

A system and method for providing telemedical direct perimetry and ophthalmoscopy to support optometric providers in the screening, diagnosis, treatment and management of glaucoma patients. The system includes an internet accessible software program inclusive of a data submission and collection module that is a menu-driven series of medical examination menus to guide clinicians through an examination procedure and data entry therefrom. In addition, a data interpretation module is provided in the form of a menu-driven series of guided menu-driven medical diagnostic menus to guide clinicians to a correct diagnosis based on a comparative analysis with visual fields and disk images. A data interpretation module is also provided and this includes an on-line library of authoritative references. A results reporting module is used for generating patient reports for glaucoma diagnosis, treatment and analysis. In addition, a unique disease management module prescribes a prioritized program of glaucoma care.

5 Claims, 43 Drawing Sheets

What is Pressure Point?

Pressure Point is a system that is designed to assist the eye care professional in the diagnosis and treatment of glaucoma. Once a patient is diagnosed with the disease, the Pressure Point system will assist the patient in the management of the disease by providing information about treatment options, late breaking news and discussion groups. Each patient that is enrolled in the system will also recieve a report that details their condition and allows the eye care professional to monitor the progression of the disease.

Pressure Point Overview

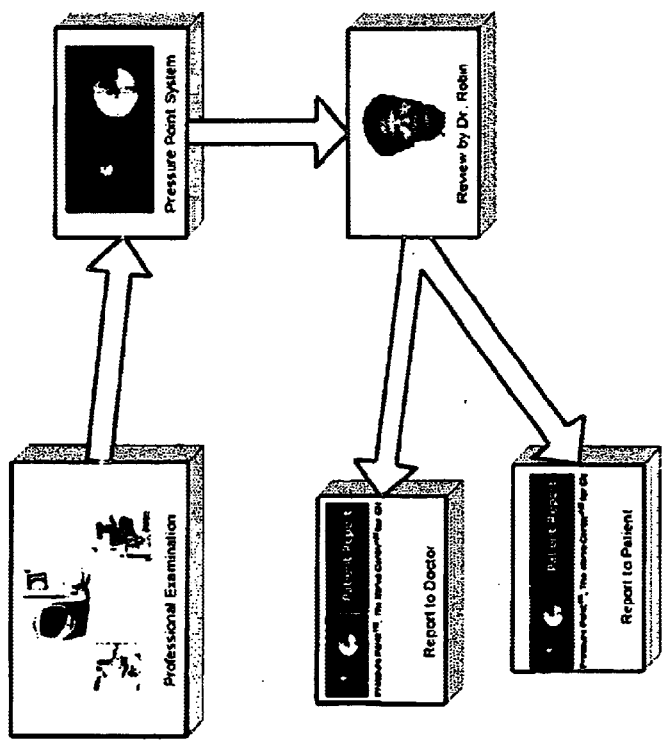

The utilization of the Pressure Point system starts in the doctor's office. The doctor will perfrom a variety of examinations that may include (but not limited to) a Slit Lamp Examination, Fundus Photography and a Perimetry Exam. Once the tests have been completed, the data is entered into the Pressure Point System. This data is then analyzed and a statistical analysis is performed that categorizes the patient's risk for the disease and provides a series of numerical ratings to various glaucoma risk factors that the eye care professional can use to track the progression of the disease. In addition, the patients record is reviewed by Dr. Alan Robin, a renowned glaucoma specialist, who will offer reccomended treatment options, medications, as well as information about the management of the disease. After the review, a report is sent to the doctor and to the patient that will remain as part of the patient's medical record.

FIG. 3

Home    Store Info    Patient Database    Help    Sample Reports

Glaucoma
Highlights

Page 1
Page 2
Page 3
page 4
Page 5
Page 6
Page 7
Page 8

GLAUCOMA Highlights

HEREDITY AND GLAUCOMA

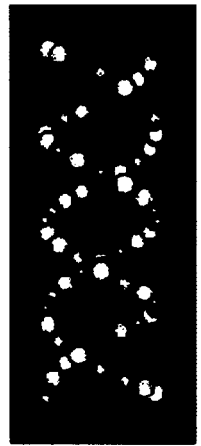

*Figure 1. DNA (deoxyribonucleic acid) provides the genetic message of the body. It has a special shape called a "double helix," due to its pair of twisted strands of genetic material.*

Glaucoma Often Occurs in Families

If you have glaucoma, there is a good chance that someone else in your family may have it, too. For primary open-angle glaucoma, the most common form of glaucoma, there is approximately a one-in-five chance that a close relative also has glaucoma. For some less common forms of glaucoma, such as Rieger's syndrome and glaucoma of childhood, the risk of brothers or sisters and children developing the disease is close to 50%. (See next page.)

FIG. 4

Pressure Point™, The Nerve Center™ for Glaucoma Treatment

Home  Store Info  Patient Database  Help  Sample Reports

Glaucoma Support Links

Support Groups
Pressure Point Chat Group
National Chat Groups
Professional Conference Room
Disease Management Pathways Select one of the links below to access a Glaucoma Support Group in your region

*Northeast*

The Glaucoma Network
National Association for Visually Handicapped (NAVH)

*Mid-Atlantic*

Glaucoma Support Group

*South*

Florida Eye Institute

*Southwest*

The Gulf Coast Glaucoma Clinic

*Midwest*

Perry Eye Clinic, Inc.

*West and Pacific Northwest*

National Association for Visually Handicapped (NAVH)

*International*

European Glaucoma Society
Royal College of Ophthalmologists
International Glaucoma Association

FIG. 5

Pressure Point™, The Nerve Center™ for Glaucoma Treatment

Home    Store Info    Patient Database    Help    Sample Reports

Glaucoma Support Links

Support Groups

Pressure Point Chat Group

National Chat Groups

Professional Conference Room

Disease Management Pathways

Q: I have been recently diagnosed as having Glaucoma and started on eye drop treatment. How long must I continue to use eye drops?
B.Y., Pheonix, Arizona A: The duration of eye drop treatment in glaucoma depends on the type of glaucoma being treated. Once eye drop treatment is initiated in the most common type of glaucoma, primary open-angle glaucoma, treatment must continue indefinitely. Eye drops which are used to reduce eye pressure have their effects for only several hours. Failure to take even one dose may cause eye pressure to increase again until such time the eye drop is taken at a later time.

Q: When should I take my eye drops?
W.C., Ellicott City, MD

A: Take your eye drops at times when they can be a part of a daily routine. Ideally, a drop which is taken four times daily should be spaced six hours apart, but often this is not practical. No one is expected to stay up late or get up early just to administer a drop. The key to successful use of eye drops is to take them every day. The best way to do this is to make the use of the drops part of a routine. It is easy to forget to take a drop, but there are certain daily routines we never forget such as waking up or going to bed, brushing teeth or bathing, eating meals, watching television or reading the paper. By associating the use of drops with one of these activities, you will be reminded to use them. Make the drops available whenever the activity takes place. If you watch TV news every night, put an extra bottle by the television. Good places for the drops might be by the bed, in the bathroom (next to a toothbrush), by the dining table, on your desk. For a once-daily drop, it is easy to remember to use it first thing in the morning. For twice-daily drops, using them first thing in the morning and before going to sleep is effective, even if the time between drops is less than or greater than 12 hours. A bottle by the bedside is a simple reminder. For an eye drop used three times a day, administer it at lunch as well as upon awakening and going to sleep. Finally, for eye drops used four times daily, using them upon awakening, at lunch, at dinner, and at bedtime is a reasonable schedule.

FIG. 6

Pressure Point™, The *Nerve Center*™ for Glaucoma Treatment

Home   Store Info   Patient Database   Help   Sample Reports

Professional Conference Room

Welcome to the Professional Conference Room - the place for recent advances, expert opinions and medications for the treatment of Glaucoma.

Return to Support Groups

Recent Advances

Ask the Expert

Overview of Medications

Preferred Practice Patterns

FIG. 7

Pressure Point™, The Nerve Center™ for Glaucoma Treatment

Home    Store Info    Patient Database    Help    Sample Reports

Professional Conference Room

Stegmann, Robert, Pienaar Anc, Miller
Viscocanalostomy for Open-Angle Glaucoma In Black African Patients
*J Cataract Refract Surg* 1999;25:316-322

Return to Support Groups

Recent Advances

Ask the Expert

Overview of Medications

Preferred Practice Patterns

Our attitudes towards the algorithm for the sequence of therapy for the patient with open angle glaucoma has changed drastically over the last decades. Compliance with medications, complications associated with medical therapy, and costs have made us reconsider the sequence of therapy. Additionally with the use of laser suture lysis, releasible sutures, and antimetabolites have increased the efficacy of filtration surgery and reduced some initial complications such as flat anterior chambers.

The frequency of the use of filtration surgery is ever increasing. However, despite these improvements, there are many problems associated with filtration surgery. The presence of a bleb is associated with wound leaks, endophthalmitis, and patient discomfort. Additionally filtration surgery is plagued with acceleration of cataract formation, choroidal detachments, and flat chambers.

Various techniques have been investigated over the last decades that could surgically decrease the intraocular pressure (IOP) without the risks of filtration surgery. Previous authors have described the use of sinusotomies and non-penetrating filtration surgery, but with limited success. The current study utilizes a novel technique of surgically lowering IOPs. ● ● ● ●

FIG. 8

Pressure Point™, The *Nerve Center*™ for Glaucoma Treatment

Home    Store Info    Patient Database    Help    Sample Reports

Professional Conference Room

Return to Support Groups

Recent Advances

Ask the Expert

Overview of Medications

Preferred Practice Patterns

Q: What are the ocular side effects of Procardia?
Dr. M. Welby, Pheonix, Arizona A: There is no effect on IOP. Side effects include: Periorbial Edema, Rotatory nystagmus, transient blindness at peak effect, retinal hemorrhages.

Q: I have a patient that is currently taking Atenolol. Are there any concerns with using this drug with an Adrenergic Agonist?
Dr. A. Quinn, Colorado Springs, CO A: When used together can cause initial hypertensive episode followed by bradycardia

FIG. 9

Pressure Point™, The Nerve Center™ for Glaucoma Treatment

Home Store Info    Patient Database    Help    Sample Reports

Cross Reactions of Systemic And Glaucoma Medications    (Current as of 8/18/1999)

| Systemic Medication | | Glaucoma Medication | | | | |
|---|---|---|---|---|---|---|
| | Generic Name (Brand Names) | Beta Blockers | Miotics | Adrenergic Agonists | Carbonic Anhydrase Inhibitors | Ocular Side Effects of Systemic Drug |
| Calcium Channel Blockers | Nifedepine (Adalat, Procardia) | Increased Risk For Severe bradycardia, a-v block, asystole, a-v block, low blood pressure | Both drugs can cause headache, nausea/vomiting, Increased vasodilation | Both drugs can cause nausea, vomiting, abdominal pain, diarrhea | Both classes can cause paresthesias, malaise, nausea, vomiting | Periorbital Edema, Rotatory nystagmus, transient blindness at peak effect, retinal hemorrhages. No effect on IOP |
| Beta-Blockers | Acebutolol (Sectral) Betaxolol (Kerlone) Metoprolol (Lopressor) Labetalol (Transdate) Nadolol (Corgard) Pindolol (Visken) Propranolol (Inderal) Timolol (Blocadren) | Both drugs can cause and make congestive heart failure worse, pulmonary edema, aggravates COPD, hyperlipoproteinemia, depression, impotence, worsening of Raynaud's phenomena | Can aggravate bronchoconstriction in patients prone to asthma, further decrease in blood pressure. Increased risk of nausea and vomiting | When used together can cause initial hypertensive episode followed by bradycardia | Both drugs can cause insomnia, dizziness, depression, nausea, and vomiting | Decrease lacrimation, lupoid syndrome, exfolatative dermatitis, myasthenic neuromuscular block. Decrease IOP. |
| ACE Inhibitors | Captopril (Capoten) Enalapril (Vasotec) Lisinopril (Prinivil) | Increased Risk for systemic hypotension. | Both drugs can cause headache. When used together can aggravate vasodilation and decrease blood pressure | Adrenergic Agonists may decrease the effect of angiotensin-converting enzyme inhibitors. | Both drugs can induce agranulocytosis | Blepharoconjunctivitis retinal hemorrhages, lupoid syndrome, exfoliative dermatitis. Decrease IOP. |
| Diuretics | Furosemide (Lasix) Hydrochlorothiazide (Hydrodiuril, Hydrodiuretic) Isradipine (Esidrix) Metalazone (Zaroxolyn) Cyclothiazide (Anhydron) Spironolactone (Aldactone) | Increased risk for systemic hypotension, both drugs can increase incidence of hyperlipoproteinemia. The combination of a thiazide diuretic and beta blockers increases blood glucose and triglyceride concentration. | Both drugs can cause headache, tremor, nausea, decreased blood pressure, diarrhea, fatigue, muscle weakness. | Can aggravate headache, palpitations when used together | Increased risk of hypokalemia, patients with hypokalemia are at higher risk for developing side effects from carbonic anhydrase inhibitors. Both drugs can ause bone marrow suppression. | Myopia, purpura, lupoid syndrome, erythema multiforme Rarely decreases IOP. |
| Cardiac Glycosides | Digoxin (Lanoxin, Lanoxicaps) Digitoxin (Crystodigin) | Increased risk of atrioventricular dissociation, cardiac arrest. Bradycardia can be potentiated. | Both drugs can cause headache, nausea, vomiting, decreased heart rate, complete heart block in high dose. | Cardiac glycosides can increase the vasoconstrictive effect adrenergic agonists. Risk of arrhythmia can be increased in digitalized patients. | Hypokalemic patients on carbonic anhydrase inhibitors are at an increased risk for developing toxic effects from cardiac glycosides. | Blue/yellow or red/green color defect, xanthopsia, angioneurotic edema, lupoid syndrome. Can decrease IOP. |

FIG. 10

Pressure Point™, The Nerve Center™ for Glaucoma Treatment

Home    Store Info    Patient Database    Help    Sample Reports

Preferred Practice Patterns

Return to Professional Conference Room

Introduction

Orientation

Background

Care Process

Care Process Management Plan

Care Process Follow-Up Glaucoma Evaluation

References

Suggested Reference Texts

Appendix 1 Suggested Medical Review Criteria

Related Academy Materials

INTRODUCTION

The development of this Preferred Practice Pattern is based on three principles:

- The Preferred Practice Pattern should be clinically relevant and specific enough to provide useful information to practitioners.

- An explicit rating of importance to the care process should be identified for each recommendation.

- An explicit rating of strength of evidence supporting each recommendation should be identified to reflect the best evidence available.

In the process of revising this Preferred Practice Pattern, a detailed literature search of articles on the subject of open-angle glaucoma published in the English language since 1985 was conducted. The results were reviewed by the Glaucoma Panel Chair and Methodologist and used to prepare the recommendations. The Panel then rated the importance to the care process for each recommendation as well as the strength of evidence in the available literature to support the recommendations made.

"Importance to the care process" represents care that the Panel thought would improve the quality of the patient's care in a meaningful way. The ratings of importance are divided into three levels, designated "A," "B" and "C," with A defined as "most important." An importance rating of B is defined as "moderately important" and of C as "relevant, but not critical."

The ratings of strength of evidence are also divided into three levels. 'I' represents ran- domized, controlled trial evidence; "II" represents the presence of evidence provided by an appropriately controlled case series and sufficient statistical analysis, at a minimum; and "III" represents consensus of expert opinion in the absence of evidence that meets criteria II. The evidence referred to is that which supports the value of the recommendation as something that should be performed to improve the quality of care. The Panel felt that it is important to readers that the strength of the evidence underlying the recommendation be made available. In this way, readers can appreciate not only how important the Panel felt each recommendation is but also understand what type of evidence supports the recommendations.

These two ratings are given in parentheses after each recommendation. For instance, (A:II) indicates a recommendation with high importance to clinical care (A), suggested by sufficiently rigorous published evidence, though not by a randomized controlled trial (II).

The sections Orientation and Background do not include recommendations; rather they are designed to educate and provide summary background information and rationale for the recommendations that are presented in the Care Process section.

FIG. 11A

Pressure Point™, The Nerve Center™ for Glaucoma Treatment

Home   Store Info   Patient Database   Help   Sample Reports

Preferred Practice Patterns

Return to Professional Conference Room

Introduction
Orientation
Background
Care Process
Care Process Management Plan
Care Process Follow-Up Glaucoma Evaluation
References
Suggested Reference Texts
Appendix 1 Suggested Medical Review Criteria
Related Academy Materials

ORIENTATION

ENTITY

Primary open-angle glaucoma (POAG), including normal-tension glaucoma (ICD-9 #365.11 and 365.12).

DEFINITION OF POAG

POAG is a multifactorial optic neuropathy in which there is a characteristic acquired loss of optic nerve fibers.

CLINICAL CHARACTERISTICS OF GLAUCOMA

POAG is a chronic, generally bilateral and often asymmetrical disease, which is characterized (in at least one eye) by all of the following:

- Evidence of glaucomatous optic nerve damage from either or both of the following:

o The *appearance of the disc or retinal nerve fiber layer* (e.g., thinning or notching of the disc rim, progressive change, nerve fiber layer defects).

o The *presence of characteristic abnormalities in the visual field* (e.g., arcuate defect, nasal step, paracentral scotoma, generalized depression) in the absence of other causes or explanations for a field defect. (See Suggested Reference Texts.)

- Adult onset

- Open, normal-appearing anterior chamber angles

- Absence of known other (e.g., secondary) causes of open-angle glaucoma

FIG. 11B

Pressure Point™, The Nerve Center™ for Glaucoma Treatment

Home   Store Info   Patient Database   Help   Sample Reports

Preferred Practice Patterns

Return to Professional Conference Room
Introduction
Orientation
Background
Care Process
Care Process Management Plan
Care Process Follow-Up Glaucoma Evaluation
References
Suggested Reference Texts
Appendix 1 Suggested Medical Review Criteria
Related Academy Materials

CARE PROCESS
Management Plan

General Principles of Therapy
Diagnosis and the approach to therapy are logical outgrowths of the ophthalmologist's integration and analysis of results of the examination and evaluation of the patient.
The diagnosis, severity of the disease, prognosis and management plan, and likelihood that therapy will be lifelong should be discussed with the patient. Glaucoma management is difficult because POAG is a chronic, frequently asymptomatic condition that commonly requires the use on a frequent basis of multiple and often expensive medications that commonly cause unwanted side effects. Establishing an effective regimen requires attention to its efficacy (potential impact on the disease) and the degree to which this is reduced by noncompliance due to visual, physical, social, economic or psychologic factors. The ophthalmologist must evaluate each of these issues and choose a regimen of maximal effectiveness for each patient.
Therapeutic Alternatives
The IOP can be lowered by medical treatment, laser surgery and other surgical approaches (alone or in combination). Medical agents that increase aqueous outflow include miotics, epinephrine compounds, alpha agonists and prostaglandins; agents that decrease aqueous production include beta adrenergic blockers and carbonic anhydrase inhibitors.
Laser trabeculoplasty increases aqueous outflow. Filtering surgery provides an alter- native path for the escape of aqueous fluid, while cyclodestructive procedures reduce the rate of aqueous production.
The choice of treatment is particularly important because glaucoma is a chronic condition, and the patient will usually require continued care for life. In addition, each form of treatment is associated with potential side effects and complications. The treatment chosen will vary with the patient's physical, visual, medical, psychological and social circumstances (A:III).56 This underscores the need for active listening and candor in patient-physician communications, record-keeping that reflects appropriate attention to these variables, and the informed consent of the patient. The choice of treatment will have as its goal the greatest potential benefit in light of the level of risk, cost and inconvenience acceptable to each individual patient. Since IOP is already less than 22 mm Hg in patients with normal-tension glaucoma, aggressive medical or early surgical intervention is often required to achieve and maintain levels of IOP at or below the target pressure. The choice of initial therapy depends on numerous considerations, and discussion of treatment should include all options (A:III). In most instances, topical medications are initial therapy (A:III). Argon laser trabeculoplasty is an appropriate initial therapy alternative (A:D,23 and filtering surgery may be an appropriate initial therapy for patients with moderate or severe glaucoma (A:I).11,12,58,59
Compliance
Medications must be effective, tolerated and taken appropriately. Adequate control of glaucoma requires a high level of compliance to therapy, which is frequently not achieved. The disease process, the rationale and goals of intervention, and the relative benefits and complications of alternative interventions should be explained to the patient so that he or she can participate meaningfully in developing an appropriate plan of action. The ophthalmologist also instructs the patient in proper techniques for taking and using medication to minimize side effects and complications (A:III). Patient education and informed participation in treatment decisions will likely improve compliance and overall effectiveness of glaucoma management. Unfortunately, studies indicate relatively poor compliance in one-third or more patients, depending on the medications employed.60,61 Poor compliance should be documented, including the patient's refusal to consent to recommended therapeutic alternatives or diagnostic procedures.

FIG. 12

Pressure Point™, The Nerve Center™ for Glaucoma Treatment

Home    Store Info    Patient Database    Help    Sample Reports

Preferred Practice Patterns

Return to Professional Conference Room

Introduction

Orientation

Background

Care Process

Care Process Management Plan

Care Process Follow-Up Glaucoma Evaluation

References

Suggested Reference Texts

Appendix 1 Suggested Medical Review Criteria

Related Academy Materials

CARE PROCESS

Follow-Up Glaucoma Evaluation

Follow-up evaluation will monitor the following components of the history and physical examination at the frequencies specified in Table 4. The recommendations apply to routine care and not to emergency visits.

| Table 4 Recommended Guidelines for Follow-up (B:III) | | | |
|---|---|---|---|
| Target IOP Achieved | Progression of Damage | Duration of Control (months) | Follow-up Interval |
| yes | no | <6 | 1-6 months |
| yes | no | >6 | 3-12 months |
| yes | yes | (n/a) | 1 week - 3 months |
| no | no | (n/a) | 1 day - 3 months |
| no | yes | (n/a) | 1 day - 1 month |

History

The following should be elicited at every routine follow-up visit:

- Interval ocular history (A:III)

- Interval systemic medical history (C:III)

- Local or systemic problems with medication (A:III)[63]

- General assessment of the impact of visual function on daily living (B:III)

- Frequency and time of last glaucoma medications (verification of appropriate use of medications) (B:II)[32,48,64,65]

Physical Examination

The following components of the physical examination should be performed at every follow-up visit:

- Visual acuity (A:III)

- IOP in both eyes (A:III)

- Slit lamp examination (A:III)

Optic nerve evaluation and recording (A:II)[45,54,55,56] and visual field evaluation (A:II)[67-70] do not need to be performed at every follow-up visit but at the recommended intervals listed in Tables 5 and 6, respectively.

| Table 5 Recommended Frequency of Optic Nerve Evaluation (A:III) | | | |
|---|---|---|---|
| Target IOP Achieved | Progression of Damage | Duration of Control (months) | Follow-up Interval |
| yes | no | <6 | 6-12 |
| yes | no | >6 | 6-18 |
| yes | yes | (n/a) | 2-6 |
| no | no | (n/a) | 2-6 |
| no | yes | (n/a) | 1-6 |

FIG. 13A

| Table 6 Recommended Frequency of Visual Field Evaluation (A:III) ||||
|---|---|---|---|
| Target IOP Achieved | Progression of Damage | Duration of Control (months) | Follow-up Interval |
| yes | no | <6 | 6-12 |
| yes | no | >6 | 6-24 |
| yes | yes | (n/a) | 3-12 |
| no | no | (n/a) | 3-12 |
| no | yes | (n/a) | 3-12 |

Within each of the above recommended intervals, factors that would favor more or less frequent evaluations include the severity of disease (mild, moderate, severe), the rate of progression, the extent to which the IOP exceeds the target value, and the number and strength of other risk factors for damage to the optic nerve. In exceptional cases, follow-up visits may be more or less frequent than the recommended intervals.

Deletion or addition of medication justifies a follow-up visit for optic nerve evaluation at the interval appropriate for wash out or maximal effect of medication withdrawn or added. Because of inherent fluctuation, variation in patient reliability and performance, visual fields often require retesting to validate apparent deterioration or to evaluate trends.

Gonioscopy

Gonioscopy is indicated when there is a suspicion of an angle-closure component or anterior chamber angle abnormalities, when miotic therapy is introduced or increased, and at least every 5 years.

FOLLOW-UP MANAGEMENT PLAN

The indications for adjusting therapy are as follows:

- A stable IOP equal to or less than the target IOP is not achieved.

- A patient continues to suffer optic nerve damage after achieving the target IOP. More comprehensive and frequent follow-up is indicated to elucidate the apparent discrepancy (e.g., diurnal IOP curves, neurologic evaluation) and reassess the validity of the diagnosis and target pressure.

- Acceptable compliance with the prescribed medical regimen is lacking.

- There is existence of stable optic nerve status and low IOP for a prolonged period in a patient on pressure-lowering medications. Under these circumstances, a carefully monitored attempt to reduce the medical regimen is appropriate.

- Contraindications to individual medicines develop.

Adjustment of target pressure downward should occur in the face of progressive disc or field change (A:II).[14,57,71,72] The extent of further reduction should be at least 20% lower than the current IOP (A:III). Upward adjustments of target pressure may occur if the patient has been stable for 5 years or more and if the patient either requires (because of side effects) or desires less medication (A:III). If a drug fails to lower IOP significantly, it should be discontinued (A:III).

Patients with POAG must receive follow-up evaluations and care to monitor and treat their disease. Guidelines for follow-up are summarized in Table 4.

Factors that affect the choice of interval within the guidelines shown include the stage of disease (more frequent for more severe disease), the degree to which the IOP exceeds the target pressure, and the number and strength of associated risk factors.

SURGICAL PROCEDURES AND POSTOPERATIVE CARE

Laser Trabeculoplasty

Laser trabeculoplasty provides a clinically significant reduction of IOP in approximately 75% of initial treatments.[23] The amount of required medical glaucoma treatment is seldom reduced after trabeculoplasty. Roughly half of patients will require additional treatment within 2 to 5 years.[23] After completing applications to the full circumference of the angle, retreatment carries a lower success rate and may carry higher risk.[73] Retreatment should be reserved for selected patients.

FIG. 13B

The surgeon must ensure that the patient receives adequate postoperative care (A:III). The plan for care prior to and after laser trabeculoplasty should contain the following elements:

Informed consent prior to surgery (A:III).[74,75]

Apraclonidine or other medications may be used perioperatively to avert IOP spikes, particularly in those patients with severe disease (A:II).[76,77]

At least one preoperative evaluation by the surgeon (A:III).

At least one IOP check within 30 to 120 minutes of surgery (A:II).[77-81]

Follow up within 2 to 3 weeks of surgery (A:III).

Follow-up examination 4 to 8 weeks postoperatively (A:II).[82-85]

Filtering Surgery

Filtering surgery often reduces IOP and, initially, the need for medical treatment. The success rate, alone or combined with medical therapy, in a previously unoperated eye averages 85% to 95% at 2 years.[86,87] While long-term control is often achieved, many patients will require re-operation or further therapy. Re-operations carry lower success rates.[88-90] In eyes that have undergone previous cataract surgery, the success rate of initial glaucoma surgery is reduced? Combined glaucoma and cataract surgery may be indicated in selected glaucoma patients who require visual rehabilitation with cataract extraction. Short-term outcome studies of combined phacoemulsifi- cation and trabeculectomy are encouraging[91,92] but long-term studies are not yet available.

Adjunctive use of antifibrosis agents (5-fluorouracil or mitomycin C improves the success (in terms of lower IOP) of repeat filtering surgery and filtering surgery in pseudophakia, aphakia and other types of complicated glaucoma. The use of adjunctive antifibrosis agents in primary filtering surgery of phakic patients appears to yield lower IOP values and to reduce the need for supplemental medical therapy. However, the use of adjunctive antifibrosis agents is associated with significant complications, for example, hypotony, which is especially likely in young myopes.[93,94] The risk-benefit ratio of use of adjunctive antifibrosis agents in primary filtering surgery cases is undetermined.

The use of seton devices (such as those described by Molteno,[95] Ahmed,[96] Kmpln[97] and others) is generally reserved for patients who have failed filtering surgery with antimetabolites or for patients whose conjunctiva is so scarred from previous surgery that filtering surgery with antimetabolites is at extraordinarily high risk for failure.

The surgeon must ensure that the patient receives adequate postoperative care (A:III). The plan for care before and after filtering surgery should include the following:

- Informed consent prior to surgery (A:II)[75]

- At least one preoperative evaluation by the surgeon (A:III).

- Use of topical corticosteroids in postoperative period, unless contraindicated (A:I).[98,99]

- The patient should be seen on the first postoperative day (12 to 36 hours after surgery) and at least once from the second to the seventh postoperative day to evaluate the visual acuity, IOP and nature of the anterior segment, including the anterior chamber angle where appropriate (A:II).[100-105]

- During a 6-week period, in the absence of complications, the plan should include two to five additional routine postoperative visits to evaluate the visual acuity, IOP and the nature of the anterior segment, including the anterior chamber angle where appropriate (A:II).[100-105]

- More frequent follow-up visits may be needed for patients with a flat or shallow anterior chamber or with postoperative complications (A:II).[100-105]

The patient and physician should be prepared to undertake additional surgical procedures to correct a flat anterior chamber, repair bleb leaks, perform suture lysis, perform bleb needling or other surgical revisions of the bleb to maximize the chances for a successful result.

FIG. 13C

Cyclodestructive Surgery

Because the outcome associated with cyclodestructive surgical procedures is less predictable and risks are greater than with other surgical procedures, these procedures are generally reserved for cases in which other modalities have failed (A:II).[75,106,107]

PROVIDER AND SETTING

The performance of certain diagnostic procedures (e.g., tonometry, perimetry and photography) may be delegated to appropriately trained and supervised personnel. How- ever, the interpretation of results and management of disease require the high degree of clinical training and experience of the ophthalmologist.

Most diagnostic and therapeutic procedures can be safely undertaken on an outpatient basis. In some instances, however, hospitalization may be required. This includes, for example, patients for whom collecting complete diurnal curves is necessary, patients whose surgical procedures are associated with a high risk of serious short-term postoperative complications, patients in whom such complications have occurred, or patients who have special medical or social needs.

COUNSELING/REFERRAL

Patients should be encouraged to alert their doctors to physical or emotional changes that occur when taking glaucoma medications. Glaucoma treatments frequently affect patient life-styles, ranging from employment issues (i.e., fear of loss of job and insurance from diminished ability to read and drive) to social issues (i.e., fear of negative impact on relationships and sexuality) to loss of independence and activities that require good visual acuity (i.e., sports and other hobbies). The ophthalmologist should be sensitive to these problems and provide support and encouragement. Where necessary, the ophthalmologist may refer the patient to peer support groups or appropriate counseling. Similarly, patients with significant visual impairment or blindness should be referred and encouraged to use appropriate low-vision and social services.

As with any condition where the diagnosis and management is in question, or where the condition is refractory to treatment, consultation with or referral to an appropriate sub- specialist may be helpful.

Pressure Point™, The Nerve Center™ for Glaucoma Treatment

Home   Store Info   Patient Database   Help   Sample Reports

Enter Store Information

| Store Information ||
|---|---|
| Store Number: 1 ||
| Street 1: | 123 Lois Lane |
| Street 2: | Kent Towers |
| City: | Metropolis |
| State: | North Carolina |
| Zip: | 31534-1123 |
| Country: | USA |

Save  Reset

FIG. 15

Pressure Point™, The *Nerve Center*™ for Glaucoma Treatment

Home    Store Info    Patient Database    Help    Sample Reports

Locate Existing Patient

When searching, the quickest way to locate a patient is to enter either the patient's SSN, Patient Number, or Pressure Point Number. If these are not available, then try the other fields.

| Locate by Patient Number or SSN | |
|---|---|
| Patient SSN: | Patient Number: |
| Pressure Point Number: | |

| Locate by Name/Date of Birth | |
|---|---|
| Last Name: | Date of Birth: |
| First Name: | |

| Locate by Store Number |
|---|
| Store Number: |

Submit   Reset

FIG. 16

Pressure Point™, The Nerve Center™ for Glaucoma Treatment

Home    Store Info    Patient Database    Patient Info    Medical Review    Examination    Submit    Help    Sample Reports

Enter Patient Information

Physician's Warning! This patient is 3 months overdue for a Visual Field Examination!

Patient Information

| | | |
|---|---|---|
| Patient Number: 1234 | SSN: 123-45-6789 | First Name: Horrible |
| Last Name: Harry | | |
| Date of Birth: 12/12/39 | ⦿ Male  ○ Female | Race: Black |

| | |
|---|---|
| Street 1: 321 Shenandoah Ct | Home Phone: (703) 555-1233 |
| Street 2: | Work Phone: (703) 555-9967 |
| City: Blacksburg | EMail: |
| State: Virginia | |
| Zip: 21043 | |
| Country: USA | |

Primary Insurance Provider:             Secondary Insurance Provider:

| | | |
|---|---|---|
| Provider: BCBS | Provider: |
| Policy Number: 99ABCD | Policy Number: |
| Group Number: 12356 | Group Number: |
| Responsible Party: Self | Responsible Party: |
| Referral: Dr. A Robin | Referral: |
| Copay: 10 | Copay: 0 |
| Relationship of Payer: Self | Relationship of Payer: |

☑ This patient has been previously diagnosed with Glaucoma.

Hidden Memo: This patient is slow to pay

FIG. 17

**Pressure Point™, The *Nerve Center*™ for Glaucoma Treatment**

Home   Store Info   Patient Database   Patient Info   Medical Review   Examination   Submit   Help   Sample Reports

Medical Review

Past Ocular History
Past Medical History
Medications
Review of Systems
Social History
Family History

| Medical History Summary |
|---|
| Relevant Medical History:   ○ Normal<br>○ Abnormal |

[Save]  [Reset]

FIG. 18

*Pressure Point*™, *The Nerve Center*™ for Glaucoma Treatment

Home   Store Info   Patient Database   Patient Info   Medical Review   Examination   Submit   Help   Sample Reports

Medical Review

Past Ocular History
Past Medical History
Medications
Review of Systems
Social History
Family History

| Past Ocular History | | | |
|---|---|---|---|
| Prior History of Glaucoma: | | Perceived Visual Loss: | |
| When Began: | 12/12/98 | When Started: | 12/12/98 |
| How Discovered: | test | When Got Worse: | 12/13/98 |
| Who Discovered: | dr robin | Describe Loss: | fast |
| Perceived Progression: | faster | | |
| Prior Medications: | | | |
| Compliance Problems: | CRS | | |
| ☐ Beta Blocker | | | |
| ☐ Prostaglandon | | | |
| ☐ Alpha-Agonist | | | |
| ☐ Carbonic Anhydrase Inhibitor | | | |
| ☐ Beta Blocker Combination | | | |
| ☐ Epinephrine | | | |

Fig. 19

Pressure Point™, The *Nerve Center*™ for Glaucoma Treatment

Home   Store Info   Patient Database   Patient Info   Medical Review   Examination   Submit   Help   Sample Reports

Medical Review

Past Ocular History
Past Medical History
Medications
Review of Systems
Social History
Family History

| Past Medical History | |
|---|---|
| ☑ Allergies to Medication | ☐ Penicillin<br>☑ Sulpha<br>☐ Other [        ] |
| ☐ Asthma | |
| ☑ Kidney Stones | |
| ☐ Carotid Disease | |
| ☐ Stroke | |
| ☐ Prior Heart Attack | |
| ☐ Depression | |
| ☐ Psychological Therapy | |
| ☐ Diabetes | |
| ☑ Hypertension | ☑ System Beta-Blockers<br>☐ Systemic Alpha Agonists<br>☐ Calcium Channel Blockers |
| ☐ Dysthyroid | |
| ☑ Migraine | |
| ☑ Poor Circulation | |

FIG. 20

Pressure Point™, The Nerve Center™ for Glaucoma Treatment

Home    Store Info    Patient Database    Patient Info    Medical Review    Examination    Submit    Help    Sample Reports

Medical Review

Past Ocular History
Past Medical History
Medications
Review of Systems
Social History
Family History

| Current Systemic Medications | |
|---|---|
| Calcium Channel Blockers | ☐ Nifedepine (Adalat, Procardia) |
| Beta-Blockers | ☐ Acebutolol (Sectral) <br> ☐ Betaxolol (Kerlone) <br> ☐ Metoprolol (Lopressor) <br> ☐ Labetalol (Transdate) <br> ☐ Nadolol (Corgard) <br> ☐ Pindolol (Visken) <br> ☐ Propranolol (Inderal) <br> ☐ Timolol (Blocadren) |
| Angiotensin-Converting Enzyme Inhibitors | ☐ Captopril (Capoten) <br> ☐ Enalapril (Vasotec) <br> ☐ Lisinopril (Prinivil) |
| Diuretics | ☐ Furosemide (Lasix) <br> ☐ Hydrochlorothiazide (Hydrodiuril, Hydrodiuretic) <br> ☐ Isradipine (Esidrix) <br> ☐ Metolazone (Zaroxolyn) <br> ☐ Cyclothiazide (Anhydron) <br> ☐ Spironolactone (Aldactone) <br> ☐ Amiloride/HCTZ (Moduretic) <br> ☐ Ethacrynic Acid (Edecrin) <br> ☐ Amiloride (Midamor) <br> ☐ Indapamide (Lozol) |
| Cardiac Glycosides | ☐ Digoxin (Lanoxin, Lanoxicaps) <br> ☐ Digitoxin (Crystodigin) |
| Aspirin | ☐ Acetylsalicyclic acid (Ascriptin, Bufferin, Bayer, Ecotrin) |
| Thyroid Supplement | ☐ Levothyroxine (Levothyroid, Synthyroid, Levoxine) <br> ☐ Liotrix (Euthroid, Thyrolar) <br> ☐ Methimazole (Tapazole) |
| Anti-Hyperglycemics | ☐ Insulin (Regular) <br> ☐ Isophane Insulin (NPH) <br> ☐ Glipizide (Glucotrol) <br> ☐ Glyburide (Diabeta, Micronase, Glynasse) <br> ☐ Tolazamide (Tolinase) <br> ☐ Tolbutamide (Orinase) <br> ☐ Chlorpropamide (Diabenase) |
| Nonsteroidal Anti-Inflammatory Drugs | ☐ Ibuprofen (Advil, Motrin) <br> ☐ Indomethacin (Indocin) <br> ☐ Naproxen (Naprosyn) |
| Estrogen/Progesterone Supplement | ☐ Estrogens (Premarin, Estratab) <br> ☐ Estradiol (Estrace, Estraderm) <br> ☐ Medroxyprogesterone (Provera) <br> ☐ Norethindrone (Aygestin) |
| Other | |

FIG. 21

**Pressure Point ™, The *Nerve Center* ™ for Glaucoma Treatment**

Home  Store Info  Patient Database  Patient Info  Medical Review  Examination  Submit  Help  Sample Reports

| Medical Review | Review of Systems | |
|---|---|---|
| Past Ocular History | ☐ Neurologic | |
| Past Medical History | ☐ Ear, Nose, and Throat | |
| Medications | ☐ Endocrine | |
| Review of Systems | ☐ Cardiovascular | |
| Social History | ☐ Circulatory | |
| Family History | | |
| | ☐ Pulmonary | |
| | ☐ GI | |
| | ☐ Skin | |
| | ☐ Psychological | |
| | ☐ GU | |
| | ☐ Musculo-skeletal | |

[Save] [Reset]

FIG. 22

Pressure Point™, The *Nerve Center*™ for Glaucoma Treatment

Home   Store Info   Patient Database   Patient Info   Medical Review   Examination   Submit   Help   Sample Reports

Medical Review

Past Ocular History
Past Medical History
Medications
Review of Systems
Social History
Family History

| Social History | |
|---|---|
| Occupation: [          ] | Hobbies:<br>☐ Reading<br>☐ Computer Work<br>☑ Driving |
| ☑ Visual Loss Interfering with Visual Function | ☐ Smokes<br>☐ Drinks |
| ☐ Able to Take Medication | ☑ Rely on Others Medication |
| Do you think patient will be compliant with medication? ○ Yes ⊙ No<br><br>Compliance Concerns:<br>[Widowed] | Other Concerns:<br>[          ] |

FIG. 23

Pressure Point™, The Nerve Center™ for Glaucoma Treatment

Home   Store Info   Patient Database   Patient Info   Medical Review   Examination   Submit   Help   Sample Reports

Medical Review

Past Ocular History
Past Medical History
Medications
Review of Systems
Social History
Family History

| Family History | |
|---|---|
| Glaucoma:<br>☑ Mother<br>☐ Father<br>☑ Granparent<br>☐ Brother/Sister<br>☐ Children<br>☐ Cousin<br>☐ Aunt/Uncle<br>☐ Other: _____ | Blindness:<br>☐ Mother<br>☐ Father<br>☐ Granparent<br>☐ Brother/Sister<br>☐ Children<br>☐ Cousin<br>☐ Aunt/Uncle<br>☐ Other: _____ |
| Cataract:<br>☐ Mother<br>☐ Father<br>☐ Granparent<br>☐ Brother/Sister<br>☐ Children<br>☐ Cousin<br>☐ Aunt/Uncle<br>☐ Other: _____ | |

FIG. 24

Pressure Point™, The Nerve Center™ for Glaucoma Treatment

Home   Store Info   Patient Database   Patient Info   Medical Review   Examination   Submit   Help   Sample Reports

Physical Exam

Physical Exam
External Examination
Pupils
Motility
Slit Lamp Exam
Gonioscopy
Optic Nerve
Perimetry

| Mental Status |
|---|
| Mental Status:  ○ Well-Oriented  ○ Not Well-Oriented |

| Eye Examination ||
|---|---|
| Right Eye: | Left Eye: |
| Vision: [20/20]  Eye Color: [Brown] | Vision: [20/20]  Eye Color: [Brown] |
| Refraction:<br>○ + [00] . [00] - [0] . [00] X [ ]<br>○ − | Refraction:<br>○ + [00] . [00] - [0] . [00] X [ ]<br>○ − |

| Intraocular Pressure ||
|---|---|
| Right Eye Pressure: | Left Eye Pressure: |
| [ ] mmHg   Instrument: [Applanation] | [ ] mmHg   Instrument: [Applanation] |

| External and Anterior Segment Examination Summary |
|---|
| Abnormal Examination Results:   ○ Yes<br>                                 ○ No |

FIG. 25

Pressure Point™, The Nerve Center™ for Glaucoma Treatment

Home   Store Info   Patient Database   Patient Info   Medical Review   Examination   Submit   Help   Sample Reports

Physical Exam

Physical Exam
External Examination
Pupils
Motility
Slit Lamp Exam
Gonioscopy
Optic Nerve
Perimetry

| Pupils | |
|---|---|
| Left Eye: | Right Eye: |
| Round, Symmetical, Reactive to Light and Accommodation<br>○ Yes<br>○ No | Round, Symmetical, Reactive to Light and Accommodation<br>○ Yes<br>○ No |

FIG. 27

Pressure Point™, The Nerve Center™ for Glaucoma Treatment

Home   Store Info   Patient Database   Patient Info   Medical Review   Examination   Submit   Help   Sample Reports

Physical Exam

Physical Exam
External Examination
Pupils
Motility
Slit Lamp Exam
Gonioscopy
Optic Nerve
Perimetry

| Motility | |
|---|---|
| Right Eye: | Left Eye: |
| ☐ Nystagmus<br>☐ ET<br>☐ XT<br>Other: | ☐ Nystagmus<br>☐ ET<br>☐ XT<br>Other: |

[Save] [Reset]

FIG. 28

Pressure Point™, The Nerve Center™ for Glaucoma Treatment

Home    Store Info    Patient Database    Patient Info    Medical Review    Examination    Submit    Help    Sample Reports

Physical Exam

Physical Exam
External Examination
Pupils
Motility
Slit Lamp Exam
Gonioscopy
Optic Nerve
Perimetry

| Slit Lamp Examination | | | |
|---|---|---|---|
| Right Eye: | | Left Eye: | |
| Conjunctiva:<br>○ Normal<br>○ Abnormal | | Conjunctiva:<br>○ Normal<br>○ Abnormal | |
| Cornea:<br>○ Normal<br>○ Abnormal | | Cornea:<br>○ Normal<br>○ Abnormal | |
| Anterior Chamber:<br>○ Normal<br>○ Abnormal | | Anterior Chamber:<br>○ Normal<br>○ Abnormal | |
| Iris:<br>○ Normal<br>○ Abnormal | | Iris:<br>○ Normal<br>○ Abnormal | |
| Lens:<br>○ Normal<br>○ Abnormal | | Lens:<br>○ Normal<br>○ Abnormal | |
| Vitreous:<br>○ Normal<br>○ Abnormal | | Vitreous:<br>○ Normal<br>○ Abnormal | |

FIG. 29

Pressure Point™, The *Nerve Center*™ for Glaucoma Treatment

Home   Store Info   Patient Database   Patient Info   Medical Review   Examination   Submit   Help   Sample Reports

Physical Exam

Physical Exam
External Examination
Pupils
Motility
Slit Lamp Exam
Gonioscopy
Optic Nerve
Perimetry

| Gonioscopy | | | |
|---|---|---|---|
| Right Eye: | | Left Eye: | |
| Angle Depth:<br>○ Normal<br>○ Deeper<br>○ Shallower | | Angle Depth:<br>○ Normal<br>○ Deeper<br>○ Shallower | |
| Other Angle Features | None | Other Angle Features | None |

FIG. 30

Pressure Point™, The Nerve Center™ for Glaucoma Treatment
Home  Store Info  Patient Database  Patient Info  Medical Review  Examination  Submit  Help  Sample Reports

| Physical Exam | Optic Nerve and Retina | | | | |
|---|---|---|---|---|---|
| | Right Eye: | | | Left Eye: | |
| | Disk Appearance | Regular Disk (No Cup) | | Disk Appearance | Regular Disk (No Cup) |
| | Cup/Disk Ratio | Horizontal: 0.0  Vertical: 0.0 | | Cup/Disk Ratio | Horizontal: 0.0  Vertical: 0.0 |
| External Examination | Abnormal Disk Features | ☐ Collateral Vessels  ☐ Diabetic  ☐ Disk Hemorrhage  ☐ Nerve Fiber Abnormality  ☐ New Disk Vessels | ☐ Notching  ☐ Pallor  ☐ Pit  ☐ Segmental  ☐ Shunt Vessels | Abnormal Disc Features | ☐ Collateral Vessels  ☐ Diabetic  ☐ Disk Hemorrhage  ☐ Nerve Fiber Abnormality  ☐ New Disk Vessels | ☐ Notching  ☐ Pallor  ☐ Pit  ☐ Segmental  ☐ Shunt Vessels |
| Pupils Motility | Macula: ○ Normal ○ Abnormal | | | Macula: ○ Normal ○ Abnormal | |
| Slit Lamp Exam | Vessels: ○ Normal ○ Abnormal | | | Vessels: ○ Normal ○ Abnormal | |
| Gonioscopy Optic Nerve | Periphery: ○ Normal ○ Abnormal | | | Periphery: ○ Normal ○ Abnormal | |

| | Optic Nerve Images | | |
|---|---|---|---|
| | Sample Images | Right Eye: | Left Eye: |
| Perimetry | | ○ Negligible Cup | ○ Negligible Cup |
| | | ○ 0.1 Cup | ○ 0.1 Cup |
| | | ○ 0.2 Cup | ○ 0.2 Cup |
| | | ○ 0.3 Cup | ○ 0.3 Cup |
| | | ○ 0.4 Cup | ○ 0.4 Cup |
| | | ○ 0.5 Cup | ○ 0.5 Cup |
| | | ○ 0.6 Cup | ○ 0.6 Cup |
| | | ○ 0.8 Cup | ○ 0.8 Cup |
| | | ○ Total Cup | ○ Total Cup |
| | | ○ Anomalous Disk | ○ Anomalous Disk |
| | | ☐ Disk Hemorrhage | ☐ Disk Hemorrhage |

FIG. 31  [Save] [Reset]

Pressure Point™, The *Nerve Center*™ for Glaucoma Treatment

Home   Store Info   Patient Database   Patient Info   Medical Review   Examination   Submit   Help   Sample Reports

Physical Exam

Physical Exam
External Examination
Pupils
Motility
Slit Lamp Exam
Gonioscopy
Optic Nerve
Perimetry Indicate Perimetric Algorithm Threshold: [SWAP]    ○ SITA
            ○ Standard Click Here to send Perimetry Data File

FIG. 32

Pressure Point™, The *Nerve Center*™ for Glaucoma Treatment

Home   Store Info   Patient Database   Patient Info   Medical Review   Examination   Submit   Help   Sample Reports

Submit this Examination

Submit

Date: [12:00:00 AM]              Doctor Number: [ ]

Data Entered By: [ ]

[SEND]  [RESET]

FIG. 33

Patient Report

Pressure Point™, The Nerve Center™ for Glaucoma Treatment
Patient Information                    Patient Name: Horrible Harry
                                       Date: November 4, 1998

Past Ocular History  The patient has been diagnosed with glaucoma for 5 years.

The patient has been noted to have increased disc cupping.

The patient is ion the following glaucoma medications:

- Xalatan 0.025%      OU BID
- Levobunolol 0.5% OU BID
- Alphagan 0.2% OU BID
- Azopt 1% OU BID
- Acetazolamide 250 mgm OU BID The patient had had the following eye surgery:

- August 1998 Argon Laser Trabeculoplasty Right Eye (360 Degrees)
- May 1997 Argon Laser Trabeculoplasty Left Eye (360 Degrees)

Past Medical History  Horrible Harry is a healthy 68 year old *African-American male*. He has a past medical History of :

- Poor circulation ( Reynaud,s Phenomenom)
- Migraine Headaches
- Systemic Hypertension
- Citrate Kidney Stones
- Sulfa allergy
- Kidney damage from prior trauma Current Systemic Medications  The Patient takes the following Systemic Medications:

- Xantac
- Inderal
- Clonidine
- Coumadin

Review of Systems  There were no relevant issues discovered during the Review of Systems.

Social History  The patient has reported the following social factors that may influence his conform to a treatment regimen:

- Widowed
- Trouble taking eye drops
- Problems with driving
- Problems with peripheral vision.

FIG. 34A

Family History   The following family members were blinded do to glaucoma:
- Mother
- Grandmother Physical         Eye Color:
Examination      RE: *Hazel*  LE: *Hazel*

Refraction:
                 RE: -0.05 + 2.50 x 030 20/30 LE: _ 1.75 x 150 20/25

Intraocular Pressure:
                 RE: 24 mm Hg Applanation   LE: 25 mm Hg Applanation External         External Examination is normal.
Examination Pupils RE: Afferent Defect   LE: No Abnormalities Motility       Motility is normal Slit Lamp              Right Eye                        Left Eye
Examination      Conjuctiva: +1 *Hyperemia*       Conjunctiva: +1 *Hyperemia*
                 Cornea: Clear                    Cornea: Clouded
                 Iris: *Early Nuclear Sclerosis*  Iris: *Early Nuclear Sclerosis*
                 Lens: Clear                      Lens: Clear Gonioscopy       RE: *Grade III Open No PAS*      LE: *Grade III Open No PAS from ALT*

Optic Nerve and  Visual Field Data:
Perimetry
                 Data                 Right Eye           Left Eye Quality of Field     Excellent           Excellent
                 Test Type            C-24-2 White        C-24-2 White
                 Color                White               White
                 Fixation             Good                Good
                 GHT                  Normal              Normal
                 MD                   -22.67              -15.89
                 PSD                  15                  14.23
                 AGIS Score           18                  16
                 CIGTS Score          10                  9

Optic Nerve:

| Disc Feature | Right Eye | Left Eye |
|---|---|---|
| Photo Quality | Good | Fair |
| Disc Size | Normal | Normal |
| Horizontal Cup: Disc | 1.0 | 1.0 |
| Vertical Cup: Disc | 0.95 | 0.9 |
| Significant Scleral Cresent | Yes | Yes |
| Disc Hemorrhage | No | No |
| Notch to Rim | Yes | Yes |

FIG. 34B

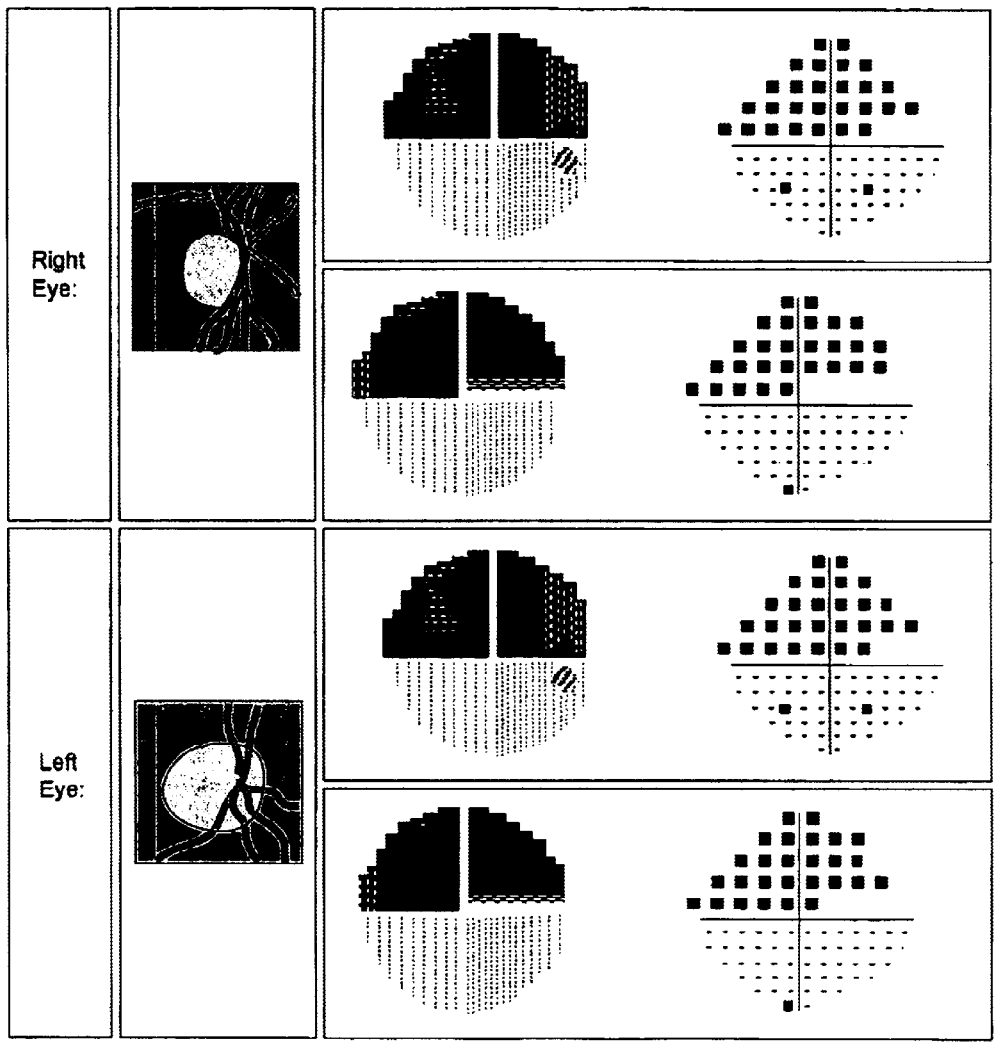

Impressions: This is a relatively young and African American patient with multiple risk factors for glaucoma. With eye pressures in the mid 20's, a family history of visual loss due to glaucoma, and markedly advanced optic nerve damage, he is at true risk of blindness with his life time. The quality of optic nerve images and visual field imagery are technically adequate. His optic nerve features are symmetrical. His visual field is symmetric. Approrpriately aggressive therapy should be undertaken.

FIG. 34C

Recommendations

- Systemic Caution! This patient is taking both a topical and systemic beta-blocker. This combination is probably not additive and has the risk of cardiac and respiratory problems secondary to excessive beta-blockade. One should evaluate the IOP lowering of the topical beta-blocker and consider eliminating this from therapy.

- Systemic Caution! This patient is taking a systemic carbonic anhydrase inhibitor with compromised renal function. One should consider eliminating the systemic acetazolamide.

- Ocular Caution! This patient is taking both a systemic and topical carbonic anhydrase inhibitor. There is probably no additive effect. The systemic carbonic anhydrase inhibitor should be removed.

- Ocular Caution! There is an approximate 10% risk of iris color change on Xanax in hazel eyes. The patient should be aware of this.

- Prognostic Risk! The AGIS study part IV has shown that African Americans still loose vision despite IOP lowering. Switching to betaxolol to timolol may offer some neuroprotective effects. Caution the patient about risks, compliance and visual loss. Advise patient about the Eye-On-Line Resource Center.

- Create a low target pressure. Either a 30% reduction (<16mm Hg.) or an IOP in the low teens would be acceptable.

- Filtration surgery is probably a good next alternative. The use of an antimetabolite is controversial, but mitomycin C might yield a lower, more prolonged IOP lowering. Remember that there is an increased risk of cataract in mitomycin C treated patients undergoing a trabeculectomy without this antimetabolite.

- Follow-up: Frequent follow-ups are recommended. After filtration surgery and the patient's stabilization, it might be wise to obtain new visual fields.

- One should rely more on perimetry than optic nerve evaluation because of marked disc structural damage. It might be difficult therefore to detect mild to moderate changes.

- One should use the C-10-2 algorithm more than the C-24-2 algorithm.

- Warning! This patient may be legally blind.

FIG. 34D

INTERNET-BASED GLAUCOMA DIAGNOSTIC SYSTEM

CROSS-REFERENCE TO RELATED APPLICATIONS

The present application derives priority from U.S. Provisional Patent Application No. 60/216,397 for "PRESSURE POINT INTERNET-BASED GLAUCOMA DIAGNOSTIC SYSTEM"; Filed: Jul. 6, 2000.

BACKGROUND OF THE INVENTION

1. Field of the Invention

The present invention relates to computer-based telemedicine systems and, more particularly, to an internet-based system to assist clinicians in the screening, diagnosis, treatment and management of glaucoma patients.

2. Description of the Background

Telemedicine systems are playing a larger role in our health care delivery system, largely in response to the demands of the market and governmental policies. This is because telemedicine has potential benefits for all parties inclusive of providers, payors and patients.

One such potential benefit is the ready access to patient medical records. Currently, this is impossible because each set of records reside at a fixed geographical location. Some providers still maintain paper records, while others rely on an electronic medical database of non-distributed (or local) design. Physicians or staff enter text information into a computer program, which then stores the data on a local or remote server that is maintained by a variety of competing vendors or the care facility itself. There is a clear need for a distributed medical database (inclusive of the method for uniform creation, accessing and updating thereof). This is especially true in the franchise setting where numerous provider franchises may be located around the world. It would be greatly advantageous in this context to provide a distributed medical information database system that allows all medical information to remain online and retrievable across geographical bounds. This would facilitate continuity of care and better medical management. Relatively few efforts have been made in this regard.

U.S. Pat. No. 5,170,362 to Greenberg et al. shows a distributed system for subjecting people such as crewmen to computer evaluations and for diagnosing their performance.

U.S. Pat. No. 5,558,638 to Evers et al. shows a comprehensive patient monitor and support system for a plurality of patients located at remote sites. At each patient site, there is a base unit, which can be connected to a number of sensors and/or recorders with sensors. The sensors are for monitoring the patient's medical state and the recorders are for recording the medical data. The base unit stores the data and transfers the data to a care center, where the data is stored and analyzed. The data retrieved from the base units is accessible on a local area network and care providers of the patients may monitor their patients by accessing the local area network.

U.S. Pat. No. 5,146,562 to Kukla shows a Patient care communication system with a plurality of communication terminals operatively coupled together for the transmission and receipt of messages.

While the above-described medical databases are "distributed", they are all centered on a single distributed network. They are not a wide area network file system capable of accommodating many franchisee networks.

Another significant advantage of telemedicine lies in improved accuracy of the examination and diagnosis procedure. Computer-guided menu-driven medical examination and diagnostic menus tend to guide clinicians through the right examination procedure and to the right diagnosis. Again, a few efforts have been made in this regard. For instance, U.S. Pat. No. 6,003,020 shows an intelligent profiling system, and U.S. Pat. No. 5,551,436 shows a medical diagnosis system which compares input data from a physician consultation to reference ranges to generate an evaluation report. Both the '436 and '020 patents suggest form-driven guided interviews. U.S. Pat. No. 5,746,204 to Schauss shows a disease analysis system which compares a database of disease symptoms to actual patient symptoms to generate a diagnosis.

U.S. Pat. No. 5,910,107 to Iliff shows a computerized medical diagnostic and treatment method for providing computerized, knowledge-based medical diagnostic and treatment advice. U.S. Pat. No. 5,437,278 to Wilk shows a medical diagnosis system that measures physical parameters of a patient (inclusive of scan images) and actually provides a diagnosis.

All of the above systems provide symptom-based diagnosis or support in the context of an expert system. There is one disease that is known as "symptom free" that would elude the prior art. Glaucoma affects approximately 2% of the population under 65 years of age and 11% over 65, and it is exceedingly difficult to diagnose and define. There is a great need for a system capable of assisting in the management, diagnosis and treatment of glaucoma. Presently, glaucoma makes up 20% of all ophthalmology business, and optometrists have been recently legislated to manage glaucoma. On the other hand, glaucoma treatment has been burdened by decreased reimbursement, and this has lead to difficulties in keeping dedicated practices current with new equipment and technologies. It would be greatly advantageous to provide a new technology in the form of a distributed system dedicated to the care and management of glaucoma. To date, there have been no known efforts to develop an internet-based system to assist clinicians in the screening, diagnosis, treatment and management in the treatment of glaucoma patients. A few computer systems offer actual patient color testing. For example, U.S. Pat. No. 5,539,482 to James et al. shows a computer glaucoma diagnostic test using visual color-pattern stimuli. However, this system is geared for direct presentation to the patient and does not assist the clinician or attending doctor in collecting information or comparing results.

It would be greatly advantageous to provide a comprehensive web-based application that is geared for use by clinicians and technicians in administering to glaucoma patients in a geographically-distributed setting. Preferably, the web application would include a guided examination and diagnosis engine incorporating a menu-driven form-based interview for guiding the technician through a patient examination, and a comparative analysis stage with images of symptoms for helping the technician to diagnose glaucoma-related problems.

SUMMARY OF THE INVENTION

In accordance with the above, it is an object of the present invention to provide an integrated software and hardware solution that uses the Internet to provide telemedical direct perimetry and ophthalmoscopy to support optometric providers in the screening, diagnosis, treatment and management of glaucoma patients.

It is another object to provide a comprehensive web-based application that is geared for use by clinicians and technicians in administering to glaucoma patients, and including a guided examination and diagnosis engine incorporating a menu-driven form-based interview for guiding the technician through a patient examination, and a comparative analysis stage with images of symptoms for helping the technician to diagnose glaucoma-related problems.

It is another object to take a glaucoma-oriented approach to both the interview and comparative analysis to ensure accurate and reliable diagnosis and prescription for the symptom free disease.

It is another object to provide timely, comprehensive glaucoma test reporting under the oversight of a renowned glaucoma specialist, such that attending clinicians can receive direction on when to refer, and how to manage care longer term In accordance with the above-described object, the present invention provides an internet-based glaucoma screening and diagnostic system to assist clinicians in the screening, diagnosis, treatment and management of glaucoma patients. The glaucoma screening and diagnostic system employs a business model designed to manage glaucoma through the following four distinct phases:

1. Data collection—an internet-based data submission module customized with computer-guided menu-driven medical examination menus to guide clinicians through the right examination procedure. This includes a distributed database with all necessary fields/history/testing requirements for glaucoma.
2. Data interpretation—a comparative data analysis module customized with computer-guided menu-driven medical diagnostic menus to guide clinicians to the right diagnosis based on a comparative analysis with visual fields and disk images, and inclusive of a comprehensive on-line library of authoritative references.
3. Results Reporting—Automated and customized report generation achieving or exceeding standard of care/best practices for glaucoma diagnosis, treatment and analysis.
4. Disease Management—An entirely new approach to glaucoma care based on a prioritized disease management model.

All four of the foregoing capabilities are integrated by the present invention into a comprehensive web-based application that is geared for use by clinicians and technicians in administering to glaucoma patients in a geographically-distributed setting.

BRIEF DESCRIPTION OF THE DRAWINGS

Other objects, features, and advantages of the present invention will become more apparent from the following detailed description of the preferred embodiment and certain modifications thereof when taken together with the accompanying drawings in which:

FIG. 3 is a screen print of the "Pressure Point" system overview.

FIG. 4 is the first of a series of "Glaucoma Highlights" informational pages on glaucoma.

FIG. 5 is a screen print of the Glaucoma Support Group page.

FIG. 6 is a screen print of the "Pressure Point Chat Group".

FIG. 7 is a screen print of the "Professional Conference Room".

FIG. 8 is an exemplary journal article as available in the "Professional Conference Room" of FIG. 7.

FIG. 9 illustrates the "Ask the Expert" discussion group function.

FIG. 10 is an exemplary breakdown of known medications for glaucoma.

FIGS. 11(A-B) illustrate the "Preferred Practice Patterns" professional management tools for institution of the preferred practice pattern.

FIG. 12 is an example of the "Care Process" screen which outlines the Care Process Management Plan.

FIGS. 13(A-D) illustrate an example of a "Care Process Follow-Up Glaucoma Evaluation.

FIG. 14 is an example of the "Disease Management Pathways" screen

FIG. 15 is a data entry screen by which member store information can be entered.

FIG. 16 is a "Locate Existing Patient" query screen.

FIG. 17 is an entry screen for new patient information.

FIG. 18 is a Search Results screen that provides the results of a patient search as well as a number of different keys by which relevant records can be sorted.

FIG. 19 is the Past Ocular History Screen.

FIG. 20 is the Past Medical History Screen.

FIG. 21 is an exemplary Medications Screen.

FIG. 22 is the Review of Systems Screen

FIG. 23 is the Social History Screen.

FIG. 24 is the Family History Screen.

FIG. 25 is the initial "Examination" screen.

FIG. 27 is the Pupils Examination Screen.

FIG. 28 is the Motility Examination Screen.

FIG. 29 is the Slit Lamp Examination Screen.

FIG. 30 is the Gonioscopy Examination Screen.

FIG. 31 is the Optic Nerve and Retina Examination Screen.

FIG. 32 is the Perimetry Screen.

FIG. 33 is the data Submission Screen.

DETAILED DESCRIPTION OF THE PREFERRED EMBODIMENT

The present invention is an internet-based system designed to assist the eye care professional in the diagnosis and treatment of glaucoma. Moreover, after a patient is diagnosed with the disease, the system assists the patient in the management of the disease by providing information about treatment options, medical news and discussion groups. As described above, the system is built around a business model designed to manage glaucoma through four distinct phases.

Figure 1:
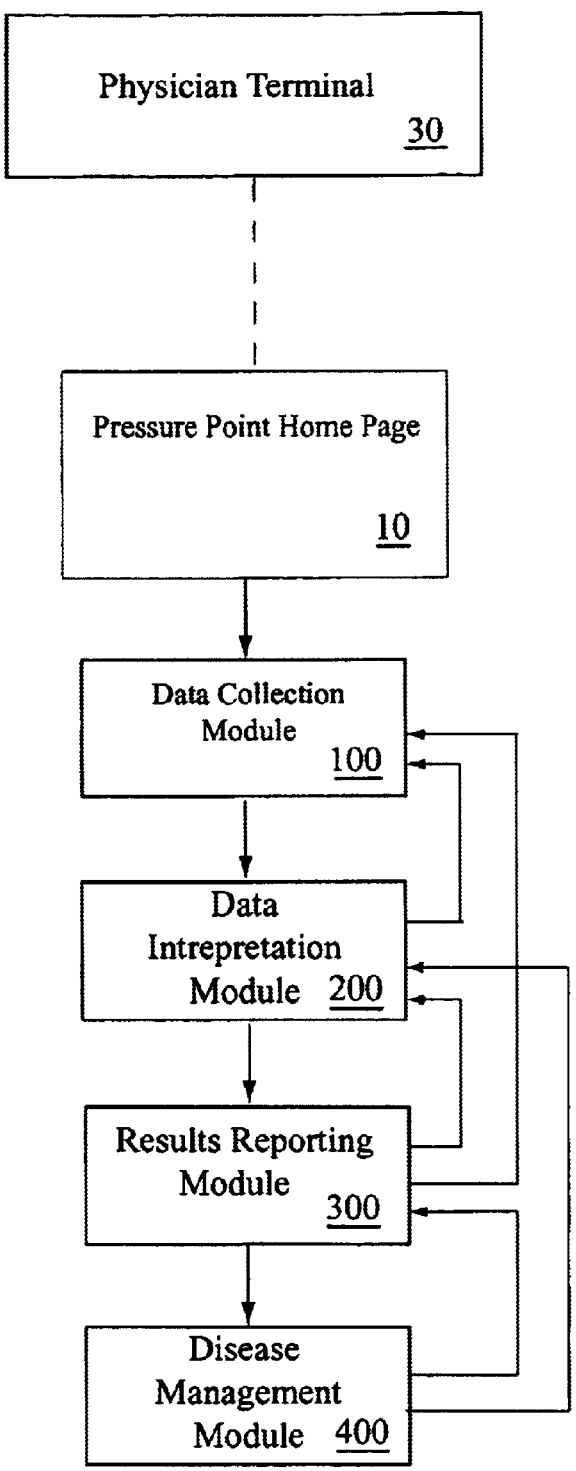
FIG. 1 is a block diagram illustrating the general organization of the Glaucoma administration system.

FIG. 1 is a block diagram illustrating the general organization of the present glaucoma administration system pursuant to the phases of Data collection, Data interpretation, Results Reporting, and Disease Management. These phases of the glaucoma administration system are accomplished by software modules.

Data Collection is accomplished by an attending physician conducting a guided medical exam and entering data at one of a plurality of networked physician terminals 30 as will be described. The data collection module 100 is an internet-accessible data submission and collection module 100 that is customized with computer-guided menu-driven medical examination menus to guide clinicians through the right examination procedure. The data submission and collection module 100 compiles a distributed database with all necessary fields/history/testing requirements for glaucoma.

Data interpretation entails a statistical analysis on the collected data that categorizes the patient's risk for the disease and provides a series of numerical ratings to various glaucoma risk factors that the eye care professional can use to track the progression of the disease. In addition, a secondary clinical review is performed remotely by a glaucoma specialist who offers recommended treatment options, medications, as well as information about the management of the disease. The data interpretation module 200 is a comparative data analysis module customized with computer-guided menu-driven medical diagnostic menus to guide clinicians through a series of considerations to the right. Visual reference images are provided along the way to give a comparative visual analysis. Data interpretation module 200 also includes a comprehensive on-line library of authoritative references to further assist in the diagnosis.

Results Reporting entails generating a report based on the foregoing steps that is sent electronically to the attending physician and to the patient that remains as part of the patient's permanent medical record. The results reporting module 300 is an automated and customized report generation program that achieves or exceeds the standard of care/best practices for glaucoma diagnosis, treatment and analysis.

Finally, disease management entails keeping the foregoing data updated at regular intervals by repeating the foregoing steps over time, and assimilating the data into a prioritized disease management model. The disease management module 400 is provided as an entirely new approach to glaucoma care based on a prioritized disease management model. Navigation of the various modules 100–400 will now be described in the context of a succession of visual displays for guiding the users through the system.

The software modules 100–400 are maintained on a central server and are remotely accessible, for example, using a conventional domain name system (DNS) for access over the internet. Once accessed, each new user must register with the system by entering their password, password confirmation, email address, user name, and title and/or other information as desired. Once registered, the user is presented with the home page screen 10 of FIG. 2.

The software method begins at this Pressure Point® home page 10 which is a top-level interface for navigating the system. From home page 10, workflow progresses in a guided manner. Specifically, the home page 10 guides a user efficiently and as needed through the data submission and collection module 100, data interpretation module 200, results reporting module 300, and disease management module 400 in any sequence. The guidance is accomplished in each case via a series of simple graphical interfaces that provide all of the software tools necessary for effective data collection, data interpretation, results reporting, and disease management. A primary advantage of the invention lies in its intuitive organization and flow.

Figure 2:
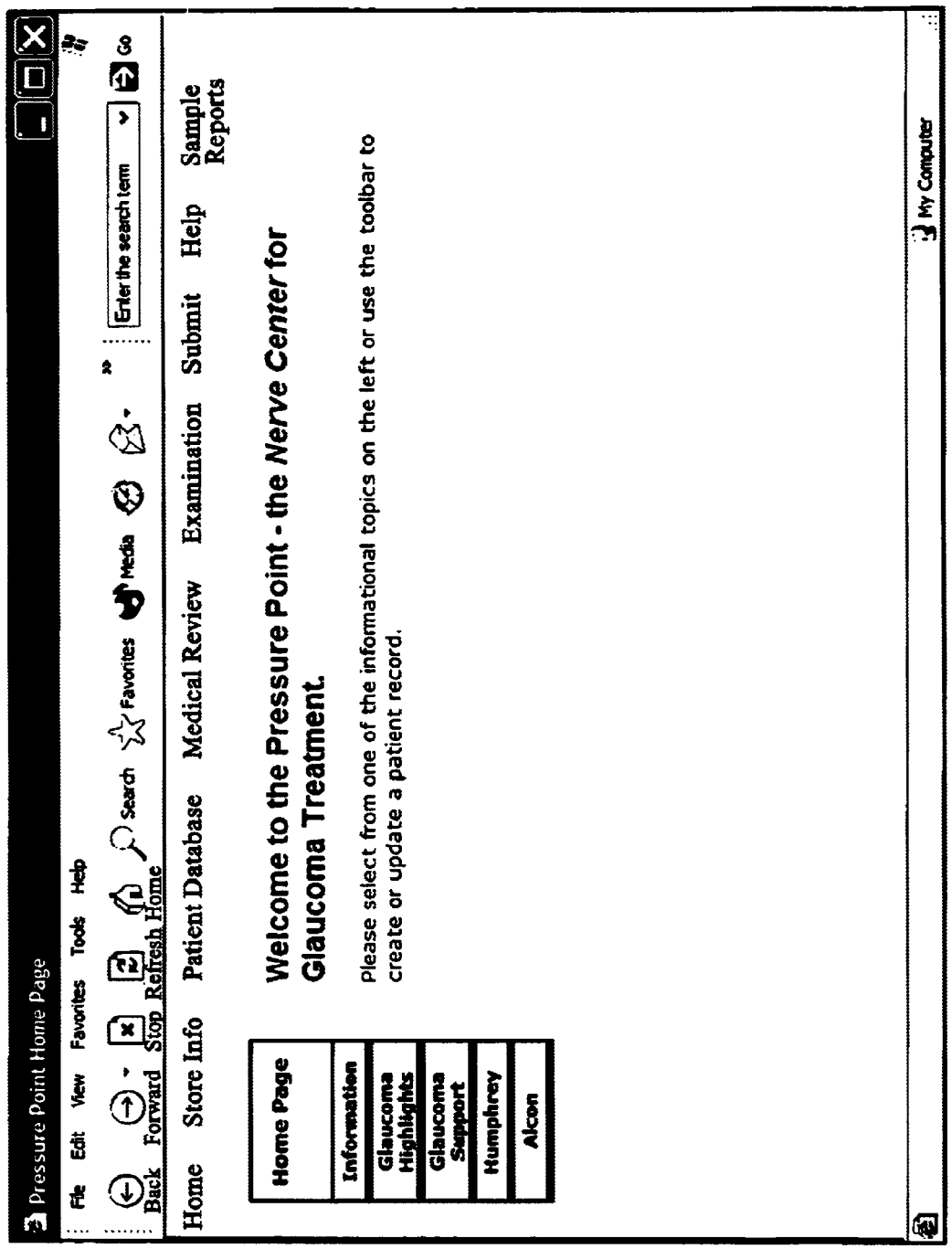
FIG. 2 is a screen print of the home page 10 which provides a user-navigable menu of content choices.

FIG. 2 is a screen print of the home page 10 which provides a user-navigable menu of content choices. The user is urged to select from a number of informational topics listed vertically on the left, or to use the horizontal toolbar to create or update a patient record. The horizontal toolbar running across the top of the screen lists destination choices including "Home", "Store Info", "Patient Database", "Help", and "Sample Reports".

Selecting "Home" directs the user to the present home page screen 10.

"Store Info" is a helpful online registry of all of all participating eye care franchises and locations as will be described.

The "Patient Database" button is integral to the data submission and collection module 100 which obtains its information via these three destination choices. More specifically, the "Patient Database" button provides access to a search engine for searching the patient medical database as compiled by the data submission and collection module 100. All necessary clinical data is defined by the clinician-user and stored in a distributed searchable online library.

Additional or different data records may be added to the library as desired.

The "Help" button invokes an on-line help function.

The "Sample Reports" button initiates the reporting module 300 which generates a variety of structured patient diagnostic and management reports as will be described.

The horizontal primary menu bar remains constant throughout navigation of the entire site, thus allowing easy access to the various modules 100, 200, 300 or 400 via the "Home", "Store Info", "Patient Database", "Help", and "Sample Reports" buttons.

Alternatively, the user can select from a variety of background informational topics and resources located below the primary menu bar and to the left. The identity of the present page is shown at the intersection of the primary menu bar and the information topics. The current page is there shown to be the "Home Page" in FIG. 2. More specifically, the information topics here available include "Information", "Glaucoma Highlights", "Glaucoma Support", "Humphrey" and "Alcon."

A wide variety of supporting information is available by pressing the "Information" button, and this action directs the user to the Information Page of FIG. 3.

Information on the Glaucoma administration system itself is available by pressing the "Information" button, and this will direct the user to the screen shown in FIG. 3, which is a screen print of the Glaucoma administration system overview. The Information screen of FIG. 3 simply provides a narrative and graphical description of the purpose and function of the present system. The horizontal primary menu bar remains constant on this screen, and the vertical menu now lists a variety of book-marked information sub-topics. The sub-topics include the reviewing specialist physician's curriculum vitae ("Here Dr. Robin CV"), information on the sponsoring care facility (Greater Baltimore Medical Center or "GBMC"), plus a "Glossary of Terms" and a "Definition of Care Givers."

Once the user has sufficient information on the system, they can return to the home page 10 of FIG. 2. Here, further information on the disease is available by pressing the "Glaucoma Highlights" button, and this will direct the user to the screen shown in FIG. 4, which is the first of a series of informational pages on glaucoma.

Once the user has sufficient information on the disease, they can return to the home page 10 of FIG. 2. Here, a variety of Glaucoma support resources are made available by pressing the "Glaucoma Support" button, and this will direct the user initially to the screen shown in FIG. 5, which is a screen print of the Glaucoma Support Group links page that geographically lists various glaucoma support links such as The Perry Eye Clinic, Inc. (Midwest), the National Association for Visually Handicapped (NAVH) (West and Pacific Northwest), and the European Glaucoma Society (International). An abundance of additional information on the disease and treatment therefor is available through these third party links. Here the user can also select from a variety of book-marked topics in this section which are named below the primary menu bar and to the left. These include a "Pressure Point Chat Group" which is a local chat room as shown in FIG. 6, whereby users can post questions and get answers. A similar "National Chat Group" function is also available. As shown in FIG. 7, the "Professional Conference Room" button leads to a web board listing of recent articles detailing advances, expert opinions and medications for the treatment of Glaucoma. In addition, the user can also select from a variety of web-board topics in this section which are named below the primary menu bar and to the left. These include "Recent Advances" such as the journal article shown in FIG. 8, an "Ask the Expert" function which is a discussion group as shown in FIG. 9, and an "Overview of Medications" which gives a comprehensive breakdown of known medications for glaucoma as shown in FIG. 10.

The disease management module 400 (FIG. 1) is accessed by the combination of the "Preferred Practice Patterns" button and the "Disease Management Pathways" button. These functions offer an entirely new approach to glaucoma care based on a prioritized disease management model and the categorical severity of the disease (mild, moderate and severe).

As shown in FIG. 11, the "Preferred Practice Patterns" button leads to an arsenal of professional management tools for institution of the preferred practice pattern, including the following book-marked sections: Introduction, Orientation, Background, Care Process, Care Process Management, Plan Care Process, Follow-Up Glaucoma Evaluation, References, Suggested Reference Texts, Appendices, Suggested Medical Review Criteria, and Related Academy Materials. As explained in FIG. 1, the disease management module 400 is based on a unique quantitative management methodology that ensures that the adapted practice pattern is clinically relevant and specific enough to provide useful information to practitioners. This is accomplished by assigning an explicit rating of importance to the care process for each recommendation, and by assigning an explicit rating of strength of evidence supporting each recommendation (to reflect the quality of evidence available). The ratings are assigned by a panel of experts, and "Importance to the care process" represents care that the panel believes would improve the quality of the patients care in a meaningful way. In accordance with the present system, the ratings of importance are divided into three levels designated "A," "B" and "C," with A defined as "most important." An importance rating of B is defined as "moderately important" and of C as "relevant, but not critical." The ratings of strength of evidence are also divided into three levels. 'I' represents randomized, controlled trial evidence; "II" represents the presence of evidence provided by an appropriately controlled case series and sufficient statistical analysis, at a minimum; and "III" represents consensus of expert opinion in the absence of evidence that meets criteria II. These categories encompass all evidence which supports the value of a recommendation as something that should be performed to improve the quality of care. The two ratings are given in parentheses after each recommendation. For instance, (A:II) indicates a recommendation with high importance to clinical care (A), suggested by sufficiently rigorous published evidence, though not by a randomized controlled trial (II). This cross-rating system offers an entirely new approach to glaucoma management.

The "Orientation" and "Background" buttons shown to the left provide summary background information and rationale for the recommendations that are presented in the "Care Process" section. For example, FIG. 12 is an "Orientation" screen for primary open-angle glaucoma (POAG), and the "Background" button leads to a comprehensive background narrative on POAG covering topics such as magnitude of the problem, epidemiology and risk factors, and screening techniques.

FIG. 12 is an example of the "Care Process" screen which outlines the Care Process Management Plan. The Care Process itself includes General Principles of Therapy, Therapeutic Alternatives, Compliance Issues, and recommended Medications.

Once the Care Process inclusive of the "Care Process Management Plan" is established, the "Care Process Follow-Up Glaucoma Evaluation" button implements the disease management model explained above with reference to FIG. 11. An example of the "Care Process Follow-Up Glaucoma Evaluation" for POAG is shown at FIG. 13. This function employs follow-up evaluations to monitor the patient history and physical examination at the frequencies specified. Note that all treatment recommendations are ranked as set forth above. As an example, the following components of the physical examination should be performed at every follow-up visit:

Visual acuity (A:III)

IOP in both eyes (A:III)

Slit lamp examination (A:III)

In this manner, a complete prioritized follow-up management plan inclusive of surgical procedures and postoperative care, provider and setting, and counseling/referral is administered.

Figure 14:
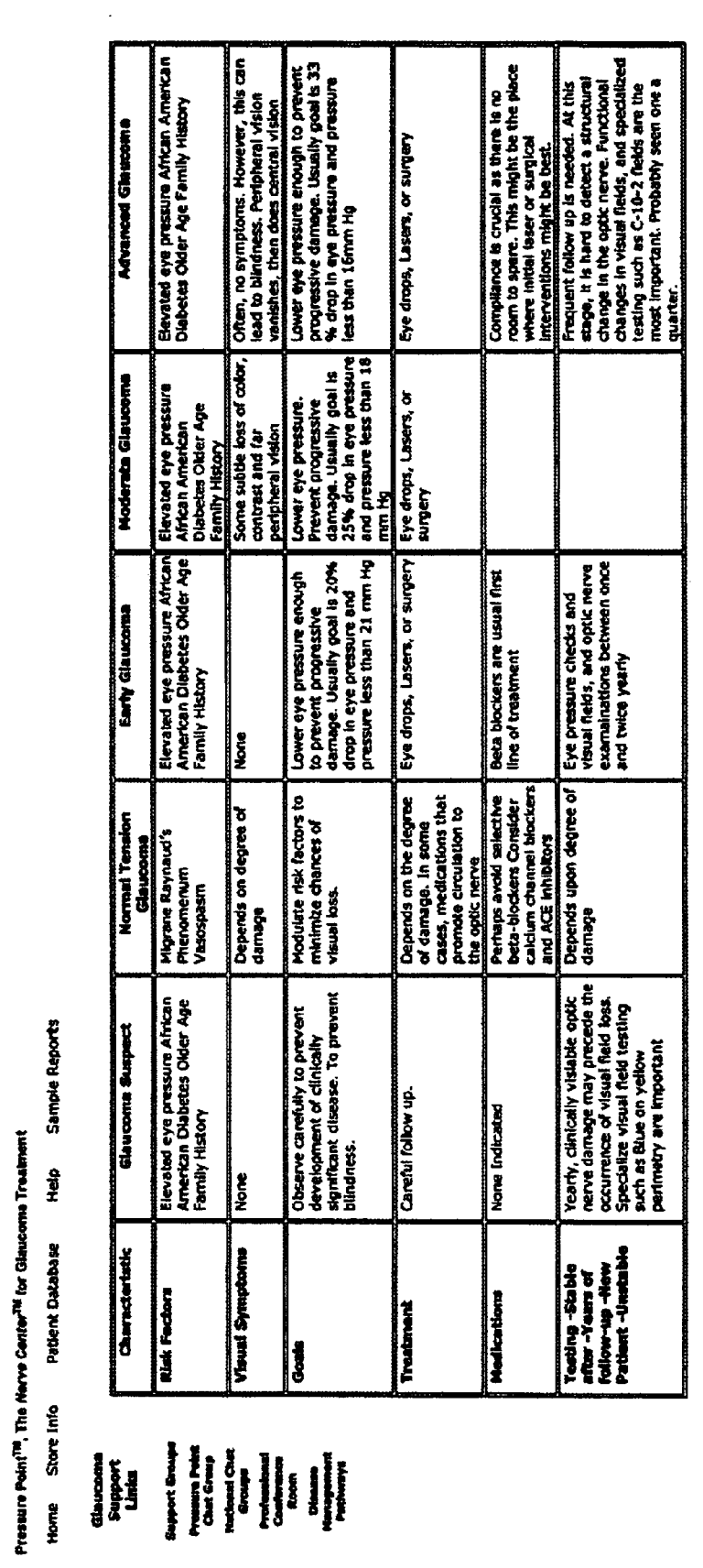

FIG. 14 is an example of the "Disease Management Pathways" screen button which is navigable by the respective button shown in FIG. 7. The "Disease Management Pathways" screen is designed as an overview of the various symptoms and management techniques for all forms of glaucoma.

Referring back to the home page of FIG. 2, the user can continue to navigate the primary tool bar by pressing the "Store Info" button, and this brings up the data entry screen of FIG. 15 by which member store or provider information can be entered. The illustrated information is saved to a database by pressing the "Save" button at bottom, or it can be reset via the "Reset" button.

Again referring back to the home page of FIG. 2, the user can depress the "Patient Database" button of the primary menu bar to access the patient medical database as compiled by the data submission and collection module 100. This provides direct access to the "Locate Existing Patient" screen show in FIG. 16, by which patient records in the database can be queried on the basis of a variety of data elements such as social security number, patient number, or name. If the user searches the database to no avail, a "no matches found" message is displayed and this automatically calls up the data entry screen of FIG. 17. Here, essential patient particulars can be entered efficiently by a combination of text entry boxes and drop-down menus. All patient information entered into the data entry screen and submitted by the "Save" button becomes a permanent record in the distributed patient information database.

If the user searches the database and a match is found, the Search Results screen of FIG. 18 is displayed. This indicates the record number and provides a link by which that record can be retrieved. The Search Results screen of FIG. 18 also provides a number of different keys by which records can be sorted (in either ascending or descending order). A disclaimer is provided at the bottom to make clear that records can become stale, and that outdated records should be reentered as new records. The option is given to call up the data entry screen of FIG. 17 for new records.

After essential patient particulars have been entered into the data entry screen of FIG. 17, and assuming that the patient has not been examined previously, the next step in completing the patient record is to conduct a "Medical Review." Given entry of the patient particulars, three additional buttons are added to the primary menu bar at the top of the screen. The first, a "Medical Review" button, initiates a menu-driven form-based interview that guides the attending technician/physician through a review of a patient's medical history. The interview begins at the Past Ocular History Screen of FIG. 19 which prompts for information such as Prior History of Glaucoma, Perceived Visual Loss:, When Started, How Discovered, etc.

Once this is completed and the data is saved, the Past Medical History Screen of FIG. 20 appears and prompts the user for Past Medical History data such as Allergies to Medication, Asthma, Kidney Stones, Carotid Disease, etc.

Once this is completed and the data saved the Medications Screen of FIG. 21 appears and prompts the user to fill in a checklist of current medications such as Beta-Blockers, Diuretics, etc. A text box at the bottom leaves room for Other miscellaneous medications.

Once this is completed and the data saved the Review of Systems Screen of FIG. 22 appears and prompts the user to fill in free form bodily systems data as shown.

Once this is completed and the data saved the Social History Screen of FIG. 23 appears and prompts the user to fill in Social History data as shown such as Occupation, Hobbies, Visual Loss Interfering with Visual Function?, Smokes?, Drinks?, etc.

Finally, the Social History data is saved the Family History Screen of FIG. 24 appears and prompts the user to fill in Family History data as shown, inclusive of check boxes of all relative who have had related eye diseases.

Given entry of the Medical Review data, the technician can depress the "Examination" button to actually begin a physical examination of the patient as administered by a menu-driven form-based interview which guides the technician through the entire physical examination and diagnosis of the patient. The physical examination is structured as a comparative data analysis with computer-guided menu-driven medical diagnostic menus to guide clinicians to the right diagnosis based on a comparative analysis with visual fields and disk images. The "Examination" begins at the Physical Examination screen of FIG. 25. Here the technician is prompted to enter comprehensive observed data inclusive of Mental Status, Eye Examination data, Vision (20/20?) And Color Vision, Intraocular Pressure, and other data elements as shown.

Figure 26:
FIG. 26 is the Physical Examination screen.

Once this data is saved, the External Examination Screen of FIG. 26 arises, prompting the technician to observe and select the condition of external features such as Lids, Lashes, and Lacrimal Apparatus from drop-down selection boxes.

Once the foregoing data is saved, the Pupils Examination Screen of FIG. 27 arises, prompting the technician to observe and indicate whether the left and right pupils are Round, Symmetical, Reactive to Light and Accommodation? This is accomplished via check boxes.

The physical examination continues through the successive Motility, Slit Lamp Exam, and Gonioscopy Screens of FIGS. 28–30, respectively.

The technician then progresses to the Optic Nerve and Retina Screen of FIG. 31, which guides the technician through a diagnosis based on a comparative analysis with visual fields and disk images. The technician is prompted for disk information such as Disk Appearance, Cup/Disk Ratio, and Disk Features. Following this, a comprehensive comparative analysis is completed with reference to actual sample images. In this manner, the technician simply compares the condition of the patient to color images exemplifying various degrees of cup from Negligible Cup to Total Cup in 0.1 increments. Other conditions such as a Disk Hemorrhage may also be viewed and selected. In each case, a high resolution color image is provided alongside each incremental check box, and the technician has only to choose the most appropriate image. It has been found through clinical trials that this unique computer-guided examination approach elevates the acumen of a technician to that of a seasoned physician.

Once the foregoing Pupils Examination data is saved, the technician is presented with the final physical examination screen and this is the Perimetry Screen of FIG. 32. Here the technician is prompted to indicate the proper threshold as well as Perimetric Algorithm (either SITA or standard).

Once the Perimetry data is entered and saved, the technician is asked to authenticate the data per the Submission Screen of FIG. 33. This screen is also offered as a choice on the primary menu bar. Date and physician data are entered and are stored along with the actual data. This completes the guided physical exam and comparative analysis stage.

Figure 34E:
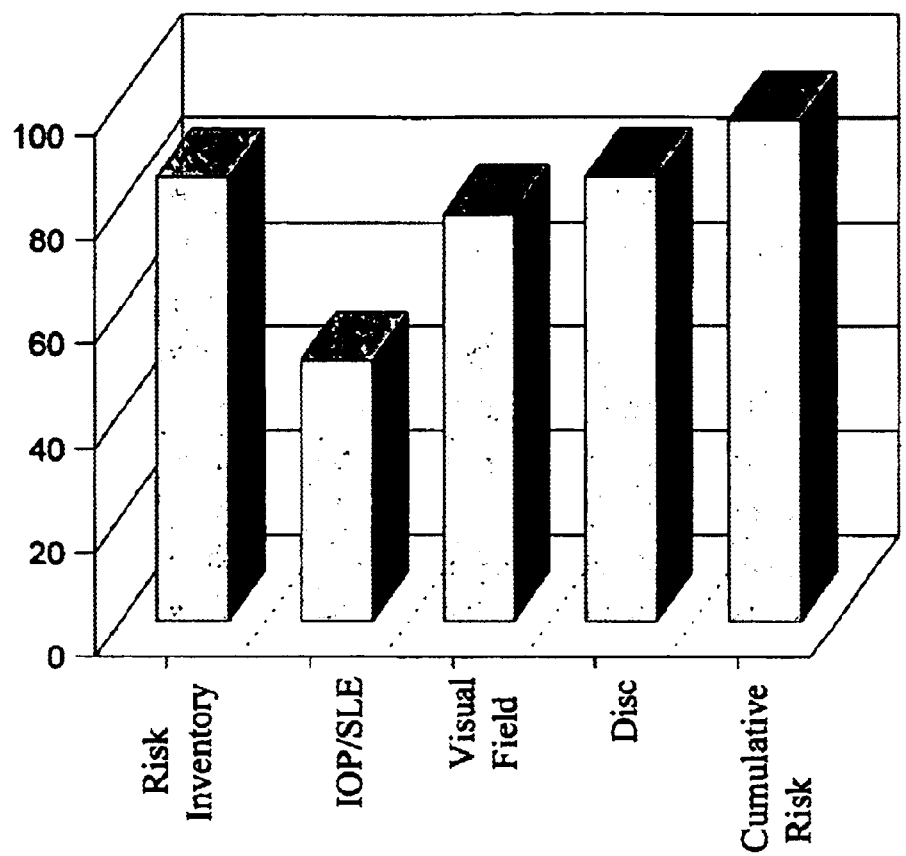
FIGS. 34(A-E) are an exemplary Patient Report Screen.

Given a patient record entered into the database in the above-described manner and coupled with a physical examination, a user can select the "Sample Reports" button from the primary menu bar (see home page of FIG. 2) to initiate the reporting module 300. Reporting module 300 is capable of generating a variety of structured patient diagnostic and management reports. An exemplary report is shown in the screen print of FIG. 34. The reporting function consolidates all directly relevant patient information into a readily comprehensible format. The report includes line items such as Past Ocular History, Past Medical History, Current Systemic Medications, and all aforementioned data elements entered during the Review of Systems, Social History, and Physical Examination. Importantly, the technician-selected nerve image sample is displayed as an integral part of the report side-by-side with the sample nerve images designated in FIG. 31 of the physical exam, and actual retinal scans. In addition, the reporting module generates a number of Cautions inclusive of systemic cautions, ocular cautions, prognostic risks, and follow-up recommendations. Finally, a Glaucoma Risk and Severity Chart is displayed as a means of graphically summarizing all of the interpreted data.

Figure 35:
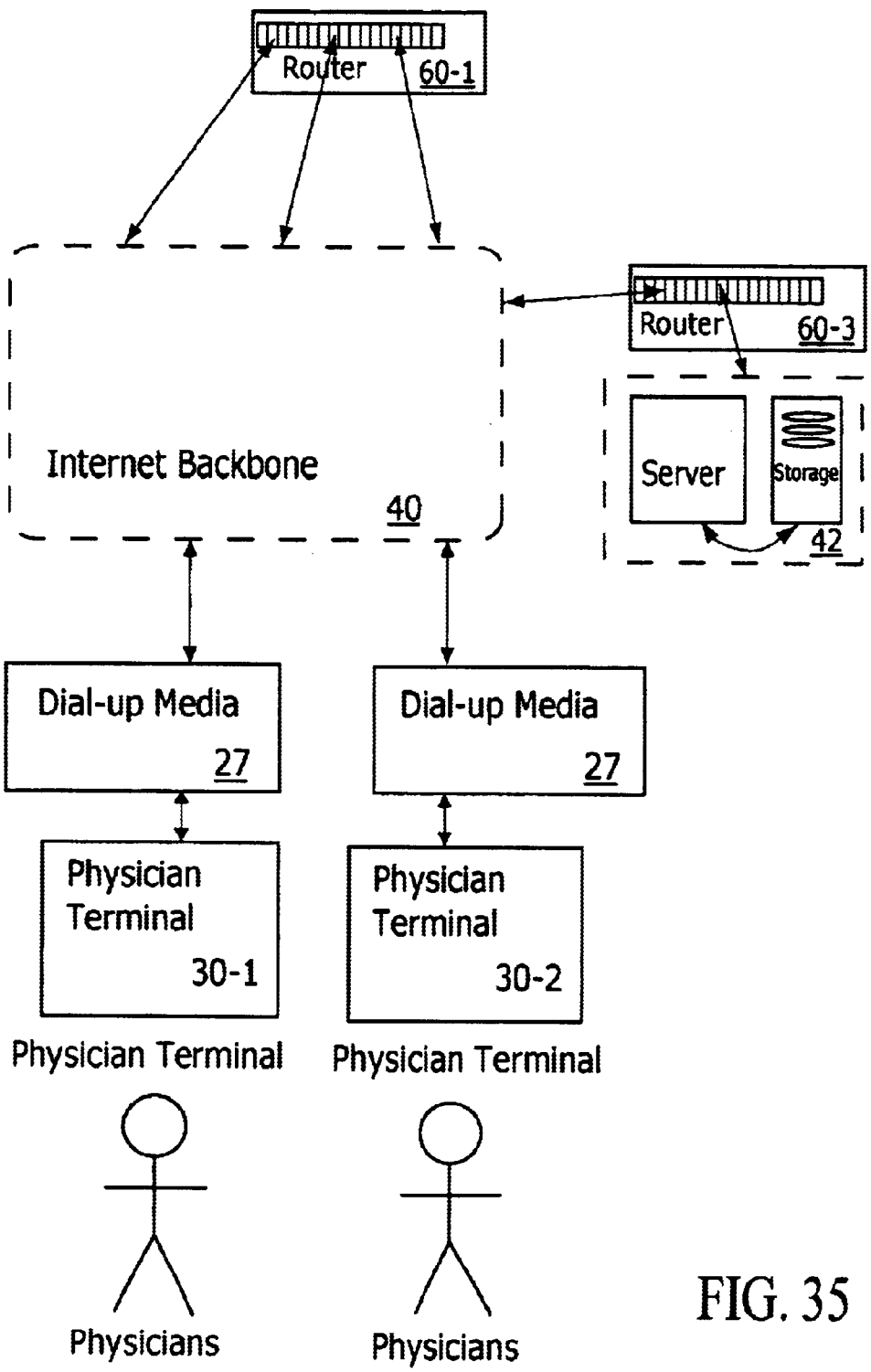
FIG. 35 is a perspective drawing of an exemplary network architecture.

FIG. 35 is a perspective drawing of an exemplary network architecture that facilitates the integrated software solution described above to provide telemedical direct perimetry and ophthalmoscopy support to optometric providers in the screening, diagnosis, treatment and management of glaucoma patients. The network architecture allows the above-described information content to be created, distributed and managed by packet-based communication.

At the lowest layer, the Glaucoma administration service is delivered through a plurality of Physician Terminals 30-1, 2 . . . n. Each Physician Terminal 30-1, 2 . . . n is a high-end computer workstation that is remotely located for convenient access by physicians (for instance, in the provider workpplace). Groups of Physician Terminals 30-1, 2 . . . n are connected by existing dialup media 27 to an existing communication backbone 40 such as the internet. A dial-up Internet backbone is presently preferred because it is the most cost-effective. Access is statistically-based as determined by a conventional router 60-1.

The distributed database is managed and maintained by a conventional server system 42 equipped with storage such as RAID memory to serve as the repository for patient records and other data. The server system 42 is likewise connected by a router 60-2 to the internet communication backbone 40. All of the software including the data submission and collection module 100, data interpretation module 200, results reporting module 300, and disease management module 400 are resident on the central server system 42.

In operation, any remotely located physician can access the software modules 100–400 and/or enter patient data directly to the central server system 42.

The above-described architecture supports dynamic and unlimited scalability, and it supports the necessary quality of service and reliability required of a mission critical real-time communication network.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

What is claimed is:

1. An objective method for helping a clinician manage a glaucoma patient, comprising the steps of:

rating the importance to the care process of a plurality of treatment options along a first scale;

rating the strength of the evidence supporting each recommendation along a second scale to reflect the quality of evidence available;

displaying said plurality of treatment options to said clinician and displaying the corresponding importance rating and strength of the evidence rating proximate thereto to assist the clinician in making glaucoma management decisions for said patient.

2. The objective method for helping a clinician manage a glaucoma patient according to claim 1, wherein said step of rating the importance to the care process further comprises assigning a categorical rating.

3. The objective method for helping a clinician manage a glaucoma patient according to claim 2, wherein said categorical rating is one from among the group of "A," "B" and "C," with A being most important and C being least important.

4. The objective method for helping a clinician manage a glaucoma patient according to claim 2, wherein said step of rating the strength of evidence further comprises assigning a categorical rating.

5. The objective method for helping a clinician manage a glaucoma patient according to claim 4, wherein said categorical rating indicates one from among the group of 1) randomized, controlled trial evidence; 2) evidence provided by a controlled case series and statistical analysis; and 3) evidence representing consensus of expert opinion.

* * * * *